United States Patent
Hawbaker et al.

(10) Patent No.: US 6,604,420 B2
(45) Date of Patent: Aug. 12, 2003

(54) NONDESTRUCTIVE ADHESION TESTING BY ULTRASONIC CAVITATION

(75) Inventors: Robert Elmer Hawbaker, Peoria, IL (US); Leonard George Wheat, Manito, IL (US); Jason William Sanders, Chillicothe, IL (US); Poh Heng Teh, Peoria, IL (US)

(73) Assignee: Caterpillar Inc, Peoria, IL (US)

( * ) Notice: Subject to any disclaimer, the term of this patent is extended or adjusted under 35 U.S.C. 154(b) by 11 days.

(21) Appl. No.: 10/025,501

(22) Filed: Dec. 26, 2001

(65) Prior Publication Data

US 2003/0115961 A1 Jun. 26, 2003

(51) Int. Cl.7 ............................................. G01N 29/00
(52) U.S. Cl. ........................................ 73/588; 73/150 A
(58) Field of Search .................... 73/588, 584, 642, 73/150 A; 427/560, 601

(56) References Cited

U.S. PATENT DOCUMENTS

| | | |
|---|---|---|
| 3,639,135 A | 2/1972 | Hohman et al. |
| 4,387,123 A | 6/1983 | Wollam et al. |
| 4,418,641 A | 12/1983 | Nakashima et al. |
| 4,501,768 A | 2/1985 | Kumar |
| 4,704,297 A | 11/1987 | Binns et al. |
| 4,843,874 A | 7/1989 | Tsuyoshi et al. |
| 4,856,326 A | 8/1989 | Tsukamoto |
| 5,045,007 A | 9/1991 | Edwards et al. |
| 5,325,713 A | 7/1994 | Furst et al. |
| 5,412,997 A | 5/1995 | Hu et al. |
| 5,454,260 A | 10/1995 | Wang |
| 5,460,859 A | 10/1995 | Reale |

Primary Examiner—John E. Chapman
(74) Attorney, Agent, or Firm—Finnegan, Henderson, Farabow, Garrett & Dunner, L.L.P.

(57) ABSTRACT

A method is provided for nondestructive adhesion testing of a coating on a component surface through ultrasonic cavitation. The disclosed method includes submerging a tip end of a vibratory horn in a liquid medium and operating a converter, coupled to the vibratory horn, at a frequency and an amplitude to generate a cavitation field within the liquid medium. A first portion of a component having an adhered coating on at least a portion of the component is moved into the cavitation field. Areas of the coating that are poorly adhered to the component are located by the removing areas of the coating that are poorly adhered, while not removing areas of the coating that are properly adhered to the component.

26 Claims, 4 Drawing Sheets

NONDESTRUCTIVE ADHESION TESTING BY ULTRASONIC CAVITATION

TECHNICAL FIELD

The invention relates generally to coatings and, more particularly, to apparatus and methods for testing the adhesion of coatings.

BACKGROUND

Surface treatments are used to alter the mechanical, electrical, thermal, optical, corrosion resistance, and wear properties of a component. Diffusion techniques generally alter the surface of the component, whereas deposition techniques cover the surface of the component with a solid material to accomplish the above. Deposition techniques include electroplating, physical vapor deposition, and chemical vapor deposition. Physical vapor deposition ("PVD") coatings, for example, are generally formed by removing atoms, ions, and/or molecules from a source and depositing the atoms on a surface of the component. Because deposition techniques result in a coating on the component surface, the altered properties of the component generally depend on complete adhesion of the coating on the surface of the component.

Testing of adhesion by indentation techniques and scratch techniques damage the coating and, thus, affect the altered property of the component. Furthermore, these techniques only test the adhesion of the coating at or near the indentation or scratch. A nondestructive technique disclosed in U.S. Pat. No. 5,454,260 attempts to overcome this problem by using a supersonic jet of water directed towards the coating. In the disclosed method, the supersonic jet of water is pre-calibrated to be slightly below the intensity that causes failure of the coating. The supersonic jet of water is then directed towards one or more sites on the coating. If the coating at the sites do not fail after impingement by the supersonic jet of water, adhesion of the coating is determined to be sufficient. One problem with the disclosed method is that it tests adhesion of the coating only at discrete sites. Another problem is that diameter of the supersonic jet of water limits testing of small components and makes testing of large components impractical.

Thus, there is a need to overcome these and other problems of the prior art and to provide an apparatus and method for adhesion testing of coatings. The present invention, as illustrated in the following description, is directed to solving one or more of the problems set forth above.

SUMMARY OF THE INVENTION

In accordance with an embodiment of the present invention, an apparatus for adhesion testing is disclosed. The apparatus includes a converter and a vibratory horn coupled to the converter, the vibratory horn having a tip end. The apparatus further includes a liquid medium in which the tip end is submerged to generate a cavitation field in the liquid medium. A stage is adapted to move a component having an adhered coating on at least a portion of the component though the cavitation field to locate areas of the coating that are poorly adhered.

Alternatively, a stage may be adapted to move the vibratory horn relative to a surface of a component to locate areas of a coating on the surface of the component that are poorly adhered.

In accordance with another embodiment of the present invention, a method for adhesion testing is disclosed. The method include submerging a tip end of a vibratory horn in a liquid medium and operating a converter, coupled to the vibratory horn, at a frequency and an amplitude to generate a cavitation field within the liquid medium. The component having a coating is moved such that the coating passes through the cavitation field. Areas of the coating that are poorly adhered to the component are located by removing the areas of the coating that are poorly adhered, while not removing areas of the coating properly adhered to the component.

In accordance with another embodiment of the present invention, a method for adhesion testing is disclosed. The method includes submerging a tip end of a vibratory horn in a liquid medium and operating a converter, coupled to the vibratory horn, at a frequency and an amplitude to generate a cavitation field within the liquid medium. The vibratory horn is moved relative to a component having a coating such that a first portion of the coating is in the cavitation field. In this manner, areas of the coating that are poorly adhered to the component are located by removing the areas of the coating that are poorly adhered, while not removing areas of the coating properly adhered to the component.

DETAILED DESCRIPTION

In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the present invention. The following description is, therefore, not to be taken in a limited sense.

Figure 1:
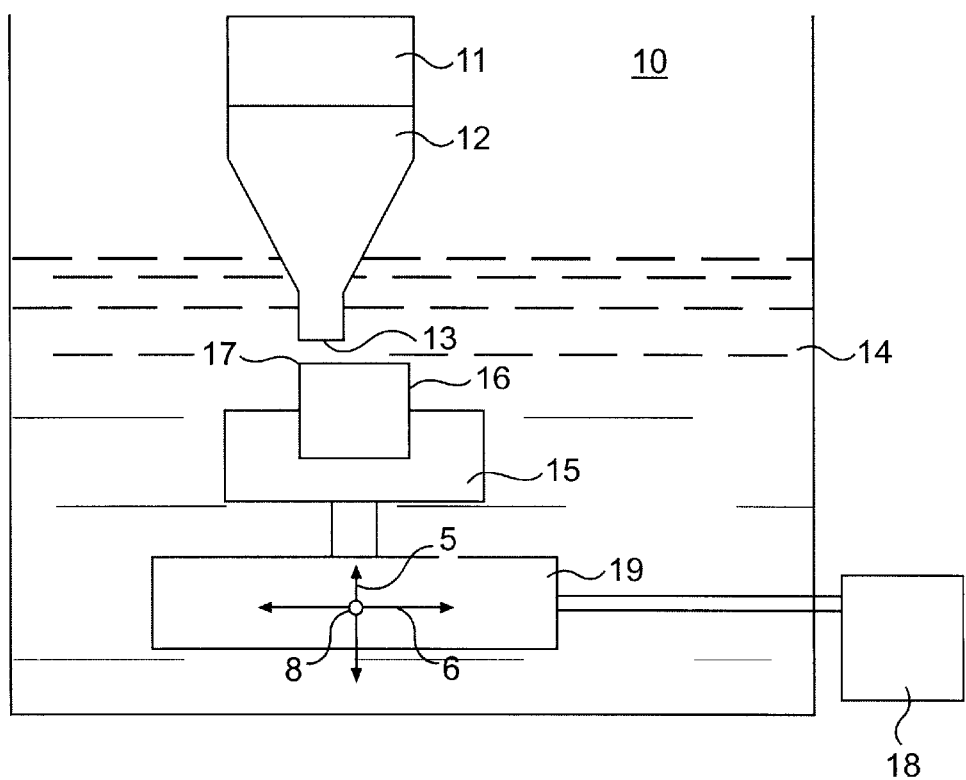
FIG. 1 is a diagrammatic representation of an apparatus for testing the adhesion of a coating consistent with an exemplary embodiment of the invention.

With reference to FIG. 1, an apparatus for adhesion testing in accordance with an exemplary embodiment of the present invention is disclosed. The apparatus, represented generally by reference numeral 10, includes converter 11, vibratory horn 12, liquid medium 14, and stage 15.

Converter 11 is a device that generates mechanical vibration at a particular frequency. Converter 11 can convert, for example, electrical energy into mechanical vibration magnetostrictively, piezoelectrically, thermally, eletrostatically, or electrodynamically. The electrical energy can be provided by, for example, a frequency generator (not shown). Converter 11 is coupled to vibratory horn 12 such that the mechanical vibration from converter 11 is transferred to vibratory horn 12. To transfer the mechanical vibration to liquid medium 14, tip end 13 of vibratory horn 12 is submerged in liquid medium 14. Liquid medium 14 is generally water and may include additives such as, for example, a corrosion inhibitor and/or a wetting agent, such as, for example, a surfactant.

Stage 15 holds component 16 so that at least a first portion of coating 17, on component 16, is within a cavitation field in liquid medium 14. Stage 15 also translates component 16 along axis 6 and/or rotates component 16 around axis 5, such that a second, adjacent portion of coating 17 can be subsequently positioned within the cavitation field. The second portion of coating 17 may overlap the first portion of coating 17.

By translating and/or rotating component 16, either constantly or in steps, so another adjacent and/or overlapping portion of coating 17 passes through the cavitation field, the adhesion of coating 17 can be scanned. In another exemplary embodiment, stage 15 rotates and/or translates component 16 along axis 8 (representing the directions into and out of the page). In yet another embodiment, stage 15 translates component along axis 5 (representing the directions up and down within the page).

Translation and/or rotation of component 16 by stage 15 can be accomplished by positioning equipment 19 known to those with skill in the art such as, for example, actuators and stepper motors. In an exemplary embodiment of the present invention, the motion of stage 15 is controlled by computer numerical control ("CNC") unit 18. In another exemplary embodiment of the present invention, the motion of stage 15 may be accomplished using computer controlled robotic positioning systems (not shown) known by those with skill in the art. The computer controlled robotic positioning system may include, for example, a computer, a controller that determines and monitors movement, and a manipulator unit that can be programmed to mechanically perform a series of automated actions.

In operation, the mechanical vibration of converter 11 is transferred to tip end 13 submerged in liquid medium 14. During one-half of each vibration cycle, a low pressure is created within liquid medium 14 thereby producing cavitation bubbles. During the other half of the vibration cycle, the bubbles collapse. The cavitation field is that volume of liquid medium 14 in which the formation and collapse of bubbles occurs. The cavitation field is influenced by, for example, vapor pressure, temperature, viscosity, and density of liquid medium 14, and the operation frequency of converter 11. These parameters may be determined by those with skill in the art. Test parameters include the distance from tip end 13 to coating 17 and the exposure time of a portion of the coating to the cavitation field. The test parameters will depend on, for example, the type and thickness of the coating 17 and the material of the underlying component. Test parameters may also be determined by those with skill in the art and will generally be sufficient to remove areas of coating 17 poorly adhered to component 16, while not removing areas of coating 17 properly adhered to component 16. As used herein, the term "properly adhered" means a coating or areas of a coating that are bonded to a component so as to impart a desired improvement to a property of the component. The term "poorly adhered" means a coating or areas of a coating that are not properly adhered to provide the desired improvement.

Figure 2:
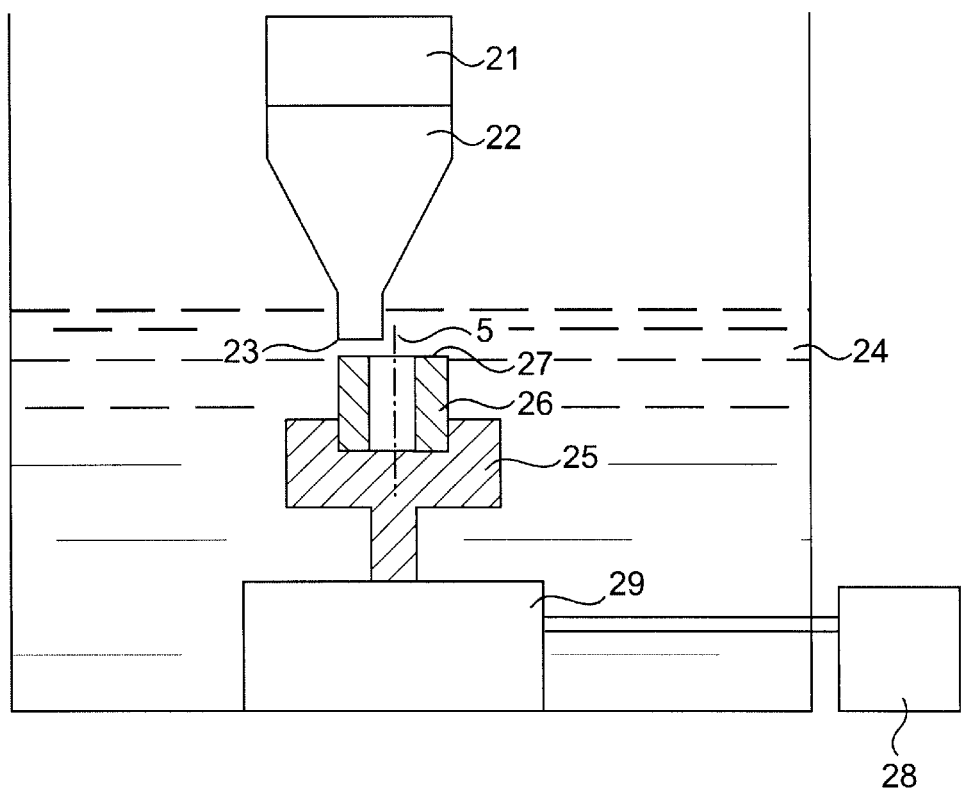
FIG. 2 is a diagrammatic representation of an apparatus for testing the adhesion of a coating consistent with an exemplary embodiment of the invention including a partial cross section.

With reference to FIG. 2, an exemplary embodiment of an apparatus and method for adhesion testing is disclosed. Converter 21, frequency generator (not shown), and vibratory horn 22 may be a single unit such as a Dismembrator unit, model number F550, available from Fisher Scientific (also available from Heat Systems, Inc. as model number XL 2020). In the exemplary embodiment, this unit may be operated at 20 kHz with an intensity control set at about 6.5 in a range from 0 to 10. Tip end 23 is about 1.27 cm in diameter.

Liquid medium 24 may be water at about room temperature and include a wetting agent such as a surfactant and corrosion inhibitor. Component 26 is, for example, a hollow steel cylinder about 7.6 cm in diameter having a wall thickness of about 2.5 cm. An end of component 26 may have chrome nitride coating 27 to provide, for example, wear and corrosion resistance to component 26. Coating 27 may be deposited by physical vapor deposition to a thickness of about 1 to 10 $\mu$m.

Stage 25 may be a three jaw chuck sold by, for example, Sherline Products, that holds component 26 such that a portion of coating 27 is about 0.1 to 5 mm from tip 23. Stage 25 continuously rotates component 26 around axis 5 so that the entirety of coating 27 is scanned through the cavitation field. Scanning may be at about 36–50 rpm for about 5 minutes. Rotation of stage 25 may be controlled by a CNC unit (not shown), stepper motor 28, and actuator 29 (also available from Sherline Products). In the disclosed embodiment, stepper motor 28 is outside a tank confining liquid medium 24, and actuator 29 is in the tank confining liquid medium 24. After scanning, areas of coating 27 poorly adhered to component 26 are removed while areas of coating 27 properly adhered to component 26 remain on component 26. In this manner, areas of coating 27 poorly adhered to component 26 are located.

Figure 3:
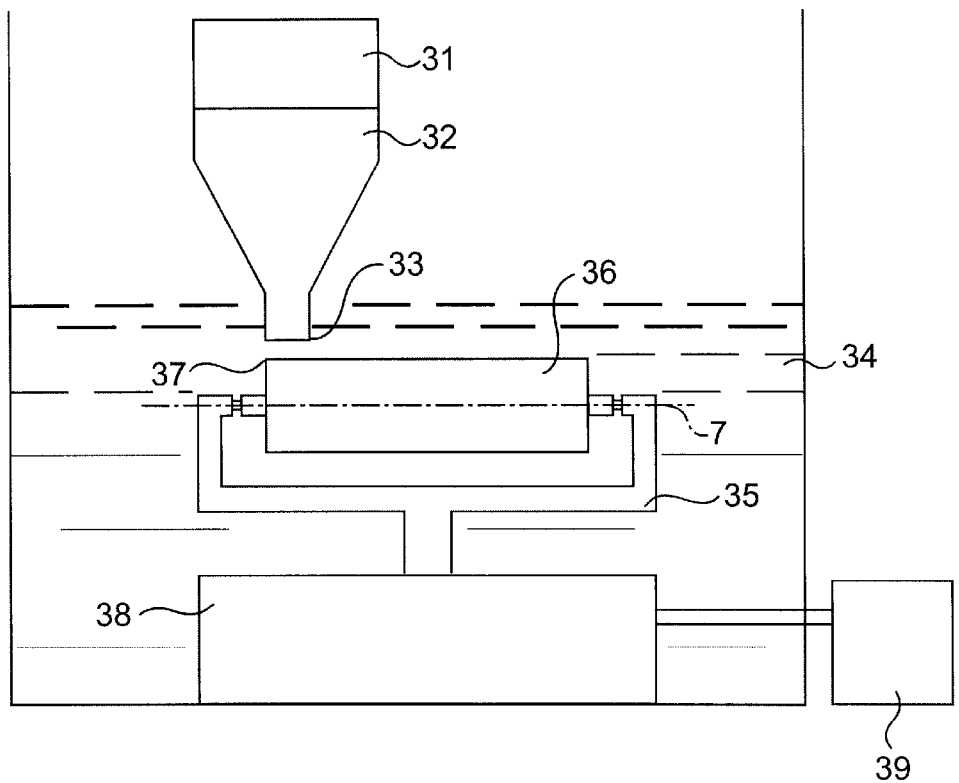
FIG. 3 is a diagrammatic representation of an apparatus for testing the adhesion of a coating consistent with another exemplary embodiment of the invention.

With reference to FIG. 3, another exemplary embodiment of an apparatus and method for adhesion testing is disclosed. Converter 31, vibratory horn 32 having tip end 33 and liquid medium 34 may be similar to that disclosed above. Component 36 may be a steel cylinder having chrome nitride coating 37 on its cylindrical surface. Stage 35 holds component 36 so that a portion of coating 37 on component 36 is about 1 mm from tip end 33. Stage 35 continuously rotates component 36 around axis 7 so that a first cylindrical portion of coating 37 is scanned through the cavitation field. Scanning may be at about 36–50 rpm for about 5 minutes. Upon completion of the scanning of the first cylindrical portion, stage 35 translates component 36 along axis 7, for example, to the left of the page, so that a second cylindrical portion of coating 37 on component 36 can be scanned. The second cylindrical portion adjoins the first cylindrical portion and may overlap the first cylindrical portion. By repeating this process, the adhesion of the entire coating on component 36 may be tested. Translation and rotation of component 36 may be accomplished by stepper motor 39 and actuator 38. Control of stepper motor 39 and actuator 38 may be by computer numerical control or computer controlled robotic positioning system known to those with skill in the art.

Figure 4:
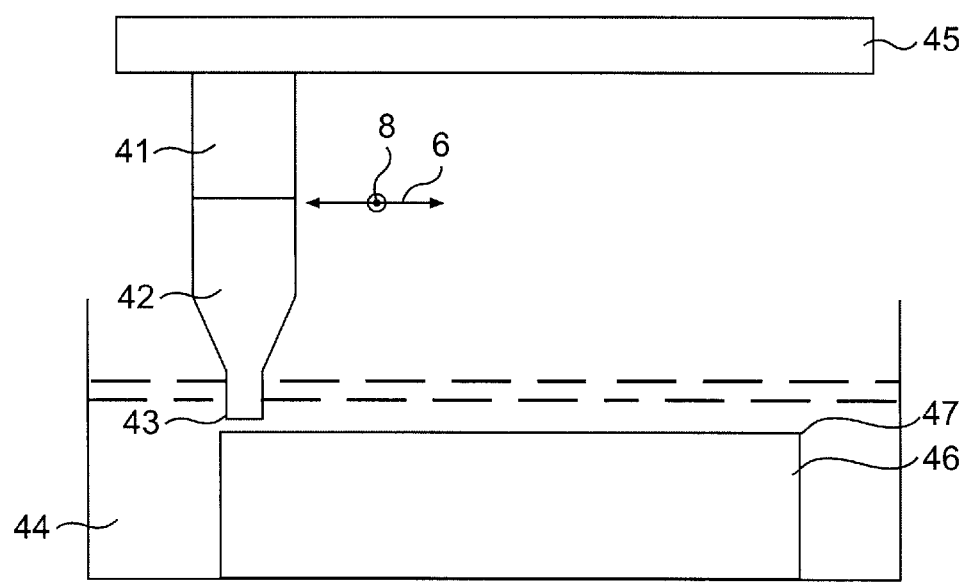
FIG. 4 is a diagrammatic representation of an apparatus for testing the adhesion of a coating consistent with still another exemplary embodiment of the invention.

With reference to FIG. 4, another exemplary embodiment of an apparatus and method for adhesion testing is disclosed. Converter 41, vibratory horn 42 having tip end 43, and liquid 44 may be similar to that disclosed above. Component 46 may be a steel component having a chrome nitride coating on its planar top surface 47. Stage 45 holds converter 41 and vibratory horn 42 so that tip end 43 is positioned about 1 mm from a first portion of top surface 47 of component 46. The first portion of top surface 47 is held within the cavitation field for about 5 minutes. Stage 45 then translates converter 41 and vibratory horn 42 along an axis 6, so that a second portion of top surface 47 is within the cavitation field. The second portion of top surface 47 adjoins and may overlap the first portion of top surface 47. By repeating this process, the adhesion of a continuous portion of the coating on top surface 47 along axis 6 may be scanned.

Stage 45 may also be adapted to translate converter 41 and vibratory horn 42 along axis 8 (going into and out of the page), so that another continuous portion of the coating on top surface 47 along axis 6 may be scanned. The another continuous portion of the coating on top surface 47 along axis 8 adjoins and may overlap the continuous portion of the coating on top surface 47 along axis 6. By repeating this process, the adhesion of the entire coating on top surface 47 may be scanned to locate poorly adhered areas.

Translation of stage 45 maybe accomplished by computer controlled robotic positioning systems know to those with skill in the art and may include, for example, a manipulator and a controller. The controller can include, for example, a computer and software to determine and monitor movement of the manipulator. The manipulator can be, for example, a mechanical unit including actuators, sensors, and grippers, or an x-y translation table.

INDUSTRIAL APPLICABILITY

The methods and apparatus according to the present invention provide the capability for nondestructive adhesion testing of coatings. Although the methods and apparatus have wide application to test coatings applied by various methods, the present invention is particularly applicable to testing adhesion of coatings applied by physical vapor deposition. Physical vapor deposition coatings are used on a variety of components to improve the component's mechanical, electrical, thermal, optical, corrosion resistance, and/or wear properties. The present invention provides methods and apparatus for testing the adhesion of a coating over a continuous portion of the component without damaging the coating. The methods and apparatus accomplish this by scanning the coating through a cavitation field that removes only poorly bonded coating. The present invention is not limited to testing only discrete portions of a component and can be adapted to test even large components of a variety of shapes.

It will be readily apparent to those skilled in this art that various changes and modifications of an obvious nature may be made, and all such changes and modifications are considered to fall within the scope of the appended claims. Other embodiments of the invention will be apparent to those skilled in the art from consideration of the specification and practice of the invention disclosed herein. It is intended that the specification and examples be considered as exemplary only, with a true scope and spirit of the invention being indicated by the following claims and their equivalents.

What is claimed is:

1. An apparatus for adhesion testing comprising:
   a converter;
   a vibratory horn coupled to the converter, the vibratory horn including a tip end;
   a liquid medium, wherein the tip end is submerged in the liquid medium to generate a cavitation field in the liquid medium; and
   a stage adapted to move a component having an adhered coating on at least a portion of the component through the cavitation field to locate areas of the coating that are poorly adhered.

2. The apparatus of claim 1, wherein the converter is at least one of magnetostrictive and piezoelectric.

3. The apparatus of claim 1, wherein the liquid medium is water including a surfactant.

4. The apparatus of claim 1, further including an actuator and a stepper motor to move the stage.

5. The apparatus of claim 4, further including a computer numerical control unit to control movement of the stage.

6. The apparatus of claim 1, further including a computer controlled robotic positioning system to control movement of the stage.

7. An apparatus for adhesion testing comprising:
   a converter;
   a liquid medium;
   a vibratory horn including a tip end submerged in the liquid medium to generate a cavitation field in the liquid medium; and
   a stage adapted to move the vibratory horn relative to a surface of a component to locate areas of a coating on the surface of the component that are poorly adhered.

8. The apparatus of claim 7, wherein the converter is at least one of magnetostrictive and piezoelectric.

9. The apparatus of claim 7, further including an actuator and a stepper motor to move the stage.

10. The apparatus of claim 9, further including a computer numerical control unit to control the actuator and stepper motor.

11. The apparatus of claim 7, further including a computer controlled robotic positioning system to move the stage.

12. A method for adhesion testing comprising:
    submerging a tip end of a vibratory horn in a liquid medium;
    operating a converter, coupled to the vibratory horn, at a frequency and an amplitude to generate a cavitation field within the liquid medium;
    moving a component having a coating such that the coating passes through the cavitation field; and
    locating areas of the coating that are poorly adhered to the component by removing the areas of the coating that are poorly adhered, while not removing areas of the coating properly adhered to the component.

13. The method of claim 12, wherein the frequency of operation of the converter is 20 MHz.

14. The method of claim 12, wherein the coating passes through the cavitation field about 0.1 to 5 mm from the tip end of the vibratory horn.

15. The method of claim 12, wherein moving the component includes rotating the component around a first axis.

16. The method of claim 12, wherein moving the component includes at least one of rotating and translating along a first axis.

17. The method of claim 16, wherein moving the component further includes at least one of rotating and translating along a second axis.

18. The method of claim 17, wherein moving the component further includes translating along a third axis.

19. The method of claim 12, wherein a continuous first and a second portion of the coating passes through the cavitation field.

20. The method of claim 12, further including mounting the component on a stage and moving the stage.

21. A method for adhesion testing comprising:
    submerging a tip end of a vibratory horn in a liquid medium;
    operating a converter, coupled to the vibratory horn, at a frequency and an amplitude to generate a cavitation field within the liquid medium; and
    moving the vibratory horn relative to a component having a coating such that a first portion of the coating is in the cavitation field; and
    locating areas of the coating that are poorly adhered to the component by removing the areas of the coating that are poorly adhered, while not removing areas of the coating properly adhered to the component.

22. The method of claim 21, wherein the vibratory horn moves along a first axis.

23. The method of claim 22, wherein the vibratory horn further moves along a second axis.

24. The method of claim 21, wherein the moving the vibratory horn is controlled by computer numerical control.

25. The method of claim 21, wherein the moving the vibratory horn is controlled by a computer controlled robotic positioning system.

26. A method for adhesion testing using ultrasonic cavitation comprising:

submerging a tip end of a vibratory horn in a liquid medium, wherein the liquid medium includes water and a surfactant;

operating a converter, coupled to the vibratory horn, at a frequency of about 20 MHz to generate a cavitation field within the liquid medium;

mounting a component having an adhered coating on a stage such that the component is about 0.1–5 mm from the tip end of the vibratory horn;

testing the adhesion of the entire coating by moving the stage so that the entire coating passes through the cavitation field.

* * * * *